United States Patent
Kong et al.

(10) Patent No.: US 10,604,455 B2
(45) Date of Patent: Mar. 31, 2020

(54) PROCESSES FOR PRODUCING AROMATIC HYDROCARBON, P-XYLENE AND TEREPHTHALIC ACID

(71) Applicants: CHINA PETROLEUM & CHEMICAL CORPORATION, Beijing (CN); SHANGHAI RESEARCH INSTITUTE OF PETROCHEMICAL TECHNOLOGY, SINOPEC, Shanghai (CN)

(72) Inventors: Dejin Kong, Shanghai (CN); Sc Edman Tsang, Shanghai (CN); Ivo Teixeria, Shanghai (CN); Qi Song, Shanghai (CN)

(73) Assignees: CHINA PETROLEUM & CHEMICAL CORPORATION, Beijing (CN); SHANGHAI RESEARCH INSTITUTE OF PETROCHEMICAL TECHNOLOGY, SINOPEC, Shanghai (CN)

( * ) Notice: Subject to any disclaimer, the term of this patent is extended or adjusted under 35 U.S.C. 154(b) by 127 days.

(21) Appl. No.: 15/291,989

(22) Filed: Oct. 12, 2016

(65) Prior Publication Data

US 2017/0101353 A1    Apr. 13, 2017

(30) Foreign Application Priority Data

Oct. 12, 2015   (CN) ........................ 2015 1 0656885

(51) Int. Cl.
| | | |
|---|---|---|
| C07C 1/207 | (2006.01) | |
| C07C 1/247 | (2006.01) | |
| C07C 51/00 | (2006.01) | |

(52) U.S. Cl.
CPC ............ C07C 1/2072 (2013.01); C07C 1/247 (2013.01); C07C 51/00 (2013.01); C07C 2529/08 (2013.01); C07C 2529/40 (2013.01); C07C 2529/65 (2013.01); C07C 2529/70 (2013.01); Y02P 20/52 (2015.11); Y02P 30/42 (2015.11)

(58) Field of Classification Search
None
See application file for complete search history.

(56) References Cited

U.S. PATENT DOCUMENTS

2013/0245316 A1* 9/2013 Masuno .................. C07C 51/16
562/409

FOREIGN PATENT DOCUMENTS

| CN | 102482177 A | 5/2012 |
|---|---|---|
| WO | 2014043468 A1 | 3/2014 |
| WO | 2014065657 A1 | 5/2014 |

OTHER PUBLICATIONS

Makarfi et al. (Chemical Engineering Journal, 2009, 154, 396).*
Yu-Ting Cheng et al.; "Production of targeted aromatics by using Diels-Alder classes of reactions with furans and olefins over ZSM-5*"; Green Chemistry, vol. 14, 2014, pp. 3114-3125.
Sara K. Green et al.; "Diels-Alder cycloaddition of 2-methylfuran and ethylene for renewable toluene"; Applied Catalysis B: Enviornmental vol. 180, 2016, pp. 487-496.
Zhaojia Lin et al.; "Aromatics from Lignocellulosic Biomass: Economic Analysis of the Production of p-Xylene from 5-Hydroxymethylfurfural", American Institute of Chemical Engineers, Jun. 2013, vol. 59, No. 6, pp. 2079-2087.
Ivo F. Teixeira et al., "From Biomass-Derived Furans to Aromatics with Ethanol over Zeolite" Angewandte Chemie, 2016, vol. 128, pp. 13255-13260.
C. Luke Williams et al., "Cycloaddition of Biomass-Derived Furans for Catalytic Production of Renewable p-Xylene", ACS Catalysis, 2012, vol. 2, pp. 935-939.
Minhua Zhang et al., "Dehydration of Ethanol to Ethylene", I & EC research Industrial & Engineering Chemistry Research, 2013, vol. 52, pp. 9505-9514.
Todsapon Thananatthanachon et al., "Efficient Production of the Liquid Fuel 2, 5-Dimethylfuran from Fructose Using Formic Acid as a Reagent", Angewandte Chemie, 2010, 122 (37), p. 6766-6768.
Siti Azmah Jambo et al., "A review on third generation bioethanol feedstock", Renewable and Sustainable Energy Reviews, 2016, 65, p. 756-769.
M. A. Ershov et al., "Prospects of bioethanol fuels E30 and E85 application in Russia and technical requirements for their quality", Renewable and Sustainable Energy Reviews, 2016, 66, p. 228-232.
Yao-Bing Huang et al., "Nickel-Tungsten Carbide Catalysts for the Production of 2, 5-Dimethylfuran from Biomass-Derived Molecules", ChemSusChem, 2014, 7 (4), p. 1068-1072.

* cited by examiner

Primary Examiner — Sudhakar Katakam
Assistant Examiner — Jennifer C Sawyer
(74) Attorney, Agent, or Firm — Novick, Kim & Lee, PLLC; Allen Xue

(57) ABSTRACT

The present invention relates to a process for preparing an aromatic hydrocarbon, and processes for producing p-xylene and terephthalic acid. The process for producing said aromatic hydrocarbon comprises a step of contacting an olefin with a diene in the presence of a catalyst to produce an aromatic hydrocarbon, which is characterized in that, at least a part of said olefin is substituted with dienophile. The reaction pressure can be reduced and the xylene selectivity can be increased with the improvement of the present invention.

19 Claims, No Drawings

PROCESSES FOR PRODUCING AROMATIC HYDROCARBON, P-XYLENE AND TEREPHTHALIC ACID

TECHNICAL FIELD

The present invention relates to a process for preparing an aromatic hydrocarbon, in particular a process for preparing an aromatic hydrocarbon product being rich in xylene. The present invention further relates to processes for preparing p-xylene and terephthalic acid based on the process for preparing said aromatic hydrocarbon.

BACKGROUND TECHNIQUE

Aromatic hydrocarbons are important basic raw materials for the petrochemical industry, and widely used in many fields such as polyester industry, chemical fiber industry, and rubber industry. Benzene, toluene and xylene are three most widely used aromatic hydrocarbons, and among others, p-xylene has the most extensive demand and application. At present, the domestic and abroad production of aromatic hydrocarbons mainly relies on the non-renewable fossil resources. However, since the fossil resources have a limited reserve and are non-renewable, the production cost for aromatic hydrocarbons are becoming higher. In addition, the continuous development and utilization of fossil resources leads to a large amount of greenhouse gas to be emitted, and a series of the resulting environmental problems are becoming more serious. Therefore, it will be meaningful and important to develop a technique of producing aromatic hydrocarbon (especially xylene) from renewable resources.

Recently, there is a certain progress in the study on the production of aromatic hydrocarbons through the biomass route. CN102482177A discloses a technique of producing p-xylene by reacting 2,5-dimethylfuran and ethylene in the presence of a catalyst. However, this technique has a problem of low xylene selectivity and high reaction pressure, which results in increasing operation complexity and risk factor. Moreover, the use of ethylene causes the consumption of fossil resource, and accordingly this technique is not completely based on the biomass route.

SUMMARY OF THE INVENTION

Based on the above-mentioned circumstance, the present inventors consider it is necessary to develop a process for preparing an aromatic hydrocarbon, which in comparison with the prior art, has a substantially comparable or even higher conversion rate of the starting material, and can remarkably reduce the reaction pressure, and thus decrease the risk factor for the operation of the reaction apparatus. Further, the present inventors also consider it is necessary to develop a process for preparing an aromatic hydrocarbon, which in comparison with the prior art, has an improved xylene selectivity and an increased xylene yield (in particular the p-xylene yield), resulting in an increased proportion of xylene in the obtained aromatic hydrocarbon product, and accordingly producing an aromatic hydrocarbon product being richer in xylene. Furthermore, the present inventor also considers it is necessary to develop a process for preparing an aromatic hydrocarbon, which in comparison with the prior art, can reduce the use of ethylene as much as possible, and even does not use ethylene, and accordingly is a completely based on biomass route.

The present inventors have found through hardworking research that one or more of the above problems in the prior art can be overcome by replacing at least a part of olefin such as ethylene with dienophile such as ethanol, and accordingly completed the present invention. Specifically, the present invention involves the following aspects:

1. (Aspect a) A process for producing an aromatic hydrocarbon by ring addition, comprising a step of contacting a starting material with a catalyst under a ring addition condition to produce an aromatic hydrocarbon stream containing benzene, toluene and xylene (named as the contacting step), wherein said starting material comprises a diene and a dienophile; or (Aspect b) A process for preparing an aromatic hydrocarbon, comprising a step of contacting an olefin with a diene in the presence of a catalyst to produce an aromatic hydrocarbon (named as the contacting step), which is characterized in that, a dienophile is used to substitute for at least a part of said olefin (preferably 5 mol % or higher, more preferably 10 mol % or higher, more preferably 20 mol % or higher, more preferably 30 mol % or higher, more preferably 40 mol % or higher, more preferably 50 mol % or higher, more preferably 70 mol % or higher, more preferably 90 mol % or higher, more preferably 95 mol % or more or the total, named as the ratio R).

According to said aspect a and said aspect b, said diene has a structural formula (I):

(I)

in formula (I), $R_1$ and $R_2$ are identical or different with each other, and selected from a group consisting of hydrogen, an optionally substituted C1-20 linear or branched alkyl, an optionally substituted C2-20 linear or branched alkenyl, an optionally substituted C2-20 linear or branched alkynyl, an optionally substituted C3-20 cycloalkyl and an optionally substituted C6-20 aryl respectively and independently; preferably selected from a group consisting of hydrogen, an optionally substituted C1-5 linear or branched alkyl and an optionally substituted C2-10 linear or branched alkenyl respectively and independently; more preferably selected from a group consisting of hydrogen and an optionally substituted C1-3 linear or branched alkyl respectively and independently, more preferably both methyl, said olefin is at least one selected from C2-C10 olefins, preferably at least one selected from C2-C10 α-olefins, more preferably at least one selected from C2-C4 α-olefins, more preferably at least one selected from ethylene and propene, more preferably ethylene, said dienophile is at least one selected from C2-C10 alcohols, preferably at least one selected from C2-C10 monohydric alcohols, more preferably at least one selected from C2-C4 alcohols or at least one selected from C2-C4 monohydric alcohols, more preferably at least one selected from ethanol, n-propanol, isopropanol and sec-butanol, more preferably ethanol.

2. The process according to any of the preceding aspects, wherein said catalyst is a molecular sieve, and said molecular sieve is one or more selected from ZSM-type molecular sieve (preferably one or more selected from ZSM-5, ZSM-11, ZSM-22, ZSM-23 and ZSM-38), Y-type molecular sieve, beta-type molecular sieve and MCM-type molecular sieve (preferably one or more selected from MCM-22 and MCM-41), preferably one or more selected from ZSM-5, Y-type molecular sieve, beta-type molecular sieve and MCM-41, more preferably ZSM-5.

3. The process according to any of the preceding aspects, wherein said ZSM-type molecular sieve (preferably ZSM-5 or ZSM-22) has a SiO2/Al2O3 molar ratio of 10-500, preferably 15-200; said Y-type molecular sieve has a SiO2/Al2O3 molar ratio of 2-80, preferably 3-50; said beta-type molecular sieve has a SiO2/Al2O3 molar ratio of 10-150, preferably 15-65; said MCM-type molecular sieve (preferably MCM-22 or MCM-41) has a SiO2/Al2O3 molar ratio of 20-250, preferably 40-150.

4. The process according to any of the preceding aspects, wherein the ratio of the mole of said diene to the total mole of said dienophile and said olefin is 0.1-10, preferably 0.5-2.

5. The process according to any of the preceding aspects, wherein said contacting step is conducted at a reaction temperature of 80 to 400° C., preferably 160 to 350° C., under a reaction pressure of 0.5 to 10 MPa, preferably 3.0 to 6.5 MPa, more preferably an autogenous pressure.

6. The process according to any of the preceding aspects, wherein said contacting step is conducted at a predetermined reaction pressure, and said pressure pressure decreases as said ratio R increases.

7. The process according to any of the preceding aspects, wherein said diene and/or said dienophile is derived from biomass material, preferably one or more derived from xylitol, glucose, cellobiose, cellulose, hemicellulose and lignin, or one or more derived from paper sludge, waste paper, sugar cane bagasse, glucose, wood, corn cobs, corn stalks and rice straw.

8. The process according to any of the preceding aspects, which further comprises a step of the biomass material being subjected to a catalytic conversion and an optional subsequent catalytic hydrogenation to produce said diene and/or said dienophile.

9. The process according to any of the preceding aspects, wherein said ring addition is conducted at a reaction temperature of 80-400° C., with a catalyst being used in an amount of 0.1-300% by weight of the starting material (i.e. the total of diene, dienophile and olefin), under a reaction atmosphere including nitrogen, hydrogen, CO2, or any mixed gas thereof.

10. A process for producing p-xylene, comprising the following steps:
a step of producing aromatic hydrocarbon with the process according to any of the preceding aspects; and
a step of separating p-xylene from said aromatic hydrocarbon.

11. A process for producing terephthalic acid, comprising the following steps:
a step of producing p-xylene with the process according to any of the preceding aspects; and
a step of converting p-xylene to terephthalic acid.

TECHNICAL EFFECT

According to one embodiment, in comparison with the prior art, the present process for producing aromatic hydrocarbon can reduce the consumption amount of olefin such as ethylene, and in a most preferable circumstance, can achieve no use of ethylene, and accordingly it is a process completely based on the biomass route.

According to one embodiment, in comparison with the prior art, the present process for producing aromatic hydrocarbon can have a substantially comparable or even higher diene conversion rate, and at the same time can remarkably reduce the reaction pressure necessary for said process; and accordingly the safety risk of the reaction apparatus is low. In a most preferable circumstance, the present process for producing aromatic hydrocarbon can be conducted under an autogenous pressure of the reaction system.

According to one embodiment, in comparison with the prior art, the present process for producing aromatic hydrocarbon can increase the initial reaction activity of diene. That is to say, the higher conversion rate for said diene can be achieved in a shorter reaction time, and accordingly the reaction time necessary for producing aromatic hydrocarbon can be shortened.

According to one embodiment, in comparison with the prior art, the present process for producing aromatic hydrocarbon can remarkably increase the conversion rate of diene, and at the same time can remarkably improve the selectivity of BTX aromatic hydrocarbons (benzene, toluene and xylene), particularly xylene, more particularly p-xylene. For example, the present process for producing aromatic hydrocarbon, the conversion rate for said diene can reach up to 99% or higher, while the selectivity for xylene (particularly p-xylene) can reach up to 87% or higher.

According to one embodiment, in comparison with the prior art, the present process for producing aromatic hydrocarbon can directly obtain an aromatic hydrocarbon product, which is substantially rich in BTX aromatic hydrocarbons (benzene, toluene and xylene), particularly xylene, wherein the content of xylene (particularly p-xylene) in the aromatic hydrocarbon product is generally larger than 30 wt %, preferably 50 wt % or higher, more preferably 70 wt % or higher, and can reach up to 94 wt %.

DETAILED DESCRIPTION OF THE INVENTION

The embodiments of the present invention will be described in detail below, but it is to be noted that the scope of the present invention is not limited by these specific embodiments, but is determined by the appended claims.

All publications, patent applications, patents, and other references mentioned in this specification are incorporated herein by reference in their entirety. Unless defined otherwise, all technical and scientific terms used herein have the same meaning as commonly understood by one of ordinary skill in the art to which this invention belongs. In the event of conflict, including the definition, the present specification shall prevail.

When the specification "known to those skilled in the art" or "conventionally known in the art" or similar terms are used to describe the materials, methods, components, devices or equipment, the term indicates the present description not only includes those routinely used at the time when the present application is filed, but also includes those not yet commonly used but are or will be suitable for the similar purpose, as recognized in the art.

In the context of this specification, unless specifically defined otherwise, conversion, yield and selectivity refer to one-way conversion, one-pass yield and one-pass selectivity, respectively.

In the context of this specification, In the context of this specification, the expression "optionally substituted" refers to being optionally substituted with one or more (e.g. 1-3, 1-2 or 1) substituent group selected from a group consisting of C1-6 linear or branched alkyl that is optionally substituted with one or more hydroxy groups or carboxyl groups; C2-6 linear or branched alkenyl that is optionally substituted with one or more hydroxy groups or carboxyl groups; C2-6 linear or branched alkynyl that is optionally substituted with one or more hydroxy groups or carboxyl groups; C3-10 cycloalkyl that is optionally substituted with one or more hydroxy groups or carboxyl groups, C6-10aryl, carboxyl and hydroxy, preferably refers to being optionally substituted with one or more (e.g. 1-3, 1-2 or 1) C1-6 linear or branched alkyl.

In the context of this specification, all percentages, parts, ratios, and the like are by weight unless otherwise expressly stated, unless a weight basis does not conform to the conventional knowledge of those skilled in the art.

In the context of the present specification, and in the absence of clearly identified, the so-called "raw" or "starting material" refers to diene, dienophile and olefin.

The present invention relates to a process for preparing an aromatic hydrocarbon, comprising a step of contacting an olefin with a diene in the presence of a catalyst to produce an aromatic hydrocarbon (contacting step). Alternatively, the present invention relates to a process for producing an aromatic hydrocarbon by ring addition, comprising a step of contacting a starting material with a catalyst under a ring addition condition to produce an aromatic hydrocarbon stream containing benzene, toluene and xylene (also referred to by contacting step).

According to the present invention, said diene generally has a structural formula (I):

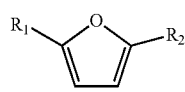

(I)

in formula (I), $R_1$ and $R_2$ are identical or different with each other, are selected from a group consisting of hydrogen, an optionally substituted C1-20 linear or branched alkyl, an optionally substituted C2-20 linear or branched alkenyl, an optionally substituted C2-20 linear or branched alkynyl, an optionally substituted C3-20 cycloalkyl and an optionally substituted C6-20 aryl respectively and independently.

According to a preferable embodiment of the present invention, in formula (I), $R_1$ and $R_2$ are identical or different with each other, are selected from a group consisting of hydrogen, an optionally substituted C1-5 linear or branched alkyl and an optionally substituted C2-10 linear or branched alkenyl respectively and independently.

According to a preferable embodiment of the present invention, in formula (I), $R_1$ and $R_2$ are identical or different with each other, are selected from a group consisting of hydrogen and an optionally substituted C1-3 linear or branched alkyl respectively and independently.

According to a preferable embodiment of the present invention, in formula (I), both $R_1$ and $R_2$ are methyl.

According to the present invention, said olefin is at least one selected from C2-C10 olefins.

According to a preferable embodiment of the present invention, said olefin is at least one selected from a group consisting of C2-C10 α-olefins, more preferably at least one selected from C2-C4 α-olefins, more preferably at least one selected from ethylene and propene, particularly ethylene.

According to the present invention, based on the prior art, the present inventors make some improvement on said contacting step, which is characterized in that, a dienophile is used to substitute for at least a part of said olefin. Here, the so-called "substitute" means that a certain amount of dienophile directly substitutes for an equal amount or a corresponding amount of olefin, and is subjected to said contacting step together with diene to produce aromatic hydrocarbon. For example, in case that it is expected in the art to an olefin in an amount of A mole(s) and a diene in an amount of B mole(s) are subjected to said contacting step, the improvement of the present invention lies in that at least a part of said olefin is replaced with dienophile, so that the olefin and the dienophile in a total amount of A mole(s) and the diene in an amount of B mole(s) are subjected to said contacting step. Therefore, based on the improvement, the present process for producing aromatic hydrocarbon comprises a step of contacting olefin (if any), dienophile and diene in the presence of a catalyst to produce aromatic hydrocarbon (also referred to by contacting step).

According to the present invention, based on the mole percent of said olefin being replaced with said dienophile (called as the ratio R), the ratio R is for example 5 mol % or higher, more preferably 10 mol % or higher, more preferably 20 mol % or higher, more preferably 30 mol % or higher, more preferably 40 mol % or higher, more preferably 50 mol % or higher, more preferably 70 mol % or higher, more preferably 90 mol % or higher, more preferably 95 mol % or more, or the total (100 mol %).

According to the present invention, said dienophile at least one selected from C2-C10 alcohols, preferably at least one selected from C2-C10 monohydric alcohols, more preferably at least one selected from C2-C4 alcohols or at least one selected from C2-C4 monohydric alcohols, more preferably at least one selected from ethanol, n-propanol, iso-propanol and sec-butanol, more preferably ethanol.

According to one embodiment of the present invention, in said contacting step, the ratio of the mole of said diene to the total mole of said dienophile and said olefin is 0.1-10, preferably 0.5-2. In particular, in case that said olefin is totally replaced with said dienophile, accordingly, the mole ratio of said diene to said dienophile is 0.1-10, preferably 0.5-2.

According to one embodiment of the present invention, the reaction temperature in said contacting step is generally 80 to 400° C., preferably 160 to 350° C.

According to the present invention, a dienophile is used to substitute for at least a part of said olefin, which in comparison with the prior art, can reduce the reaction pressure necessary for the contacting step. Specifically, as said ratio R increases, the pressure as high as expected in the art is unnecessarily used, and said reaction pressure can be accordingly reduced. In this aspect, there is not a particular limitation on the reduction extent for the reaction pressure as the ratio R increases, and it is enough if the pressure reduction is substantial for those skilled in the art. For example, said ratio R increases by each 5 mol %, said reaction pressure (compared with the prior art) generally reduces by 5% or higher, preferably by 10% or higher. For example, if completely using ethanol as dienophile, the reaction pressure is 3.4 MPa, while for completely using ethylene as the starting material of the reaction, the pressure is 7.5 MPa, and accordingly relative to the reaction under 3.4 MPa of completely using ethanol, the pressure reduces by 120%; for a reaction system of 50% ethylene+50% ethanol, the pressure reduces by 60%. More particularly, the reaction pressure of said contacting step is generally 0.5 to 10 MPa, preferably 3.0 to 6.5 MPa. In a most preferable case, said contacting step is conducted under an autogenous pressure of the reaction system.

According to the present invention, a dienophile is used to substitute for at least a part of said olefin, which in comparison with the prior art, can increase the initial reaction activity of said diene. That is to say, a higher conversion rate for said diene can be achieved in a shorter reaction time, and accordingly reduces the reaction time necessary for producing aromatic hydrocarbon. Specifically, as said ratio R increases, the reaction time as long as expected in the art is unnecessarily used, and said reaction time can be accordingly reduced. In this aspect, there is not a particular limitation on the reduction extent for the reaction time as the ratio R increases, and it is enough if the time reduction is substantial for those skilled in the art. For example, said ratio R increases by each 5 mol %, said reaction pressure (compared with the prior art) generally reduces by 5% or higher, preferably by 10% or higher. In Example 1, after one hour of the reaction, the conversion rate can be 60%, while in Comparative Example 1, in which only ethylene is used as dienophile, the conversion rate can be 18%, and the reaction continues for 24 hours, and the conversion rate for Comparative Example 1 is only 54%, and it is a conversion lower than 60%. In contrast, the addition of alcohol can reduce the reaction time. More particularly, the reaction time of said contacting step is generally 1 to 24 hrs, preferably 1 to 6 hrs.

According to the present invention, said contacting step can be conducted in a continuous manner or in a batch manner. There is no particular limit. In the continuous manner, the weight space velocity of said reaction material is generally 0.1 to 10 $hr^{-1}$, preferably 0.5 to 4 $hr^{-1}$. In the batch manner, the used amount of the catalyst is generally 0.1-300 wt %, preferably 1 to 30 wt % of the used amount of the reaction material (referring to the total amount of diene, dienophile and olefin by weight).

According to one embodiment of the present invention, said diene (particularly 2,5-dimethylfuran) can be derived from biomass material. As said biomass material, for example, those commonly used in the art for producing aromatic hydrocarbon can be listed out. Specifically, xylitol, glucose, cellobiose, cellulose, hemicellulose, lignin and the like can be listed out. These biomass materials can be used alone, or a combination of two or more can be used.

According to one embodiment of the present invention, said dienophile (particularly ethanol or isopropanol) can be derived from biomass material. As said biomass material, for example, those commonly used in the art for producing aromatic hydrocarbon can be listed out. Specifically, xylitol, glucose, cellobiose, cellulose, hemicellulose, lignin and the like can be listed out. These biomass materials can be used alone, or a combination of two or more can be used.

According to another embodiment of the present invention, as said biomass material, for example, paper sludge, waste paper, sugar cane bagasse, glucose, wood, corn cobs, corn stalks, rice straw and the like can be also listed out. These biomass materials can be used alone, or a combination of two or more can be used. Here, based on the weight percent, said biomass material has a cellulose content of usually 30-99%, a hemicellulose content of usually 0-50%, and a lignin content of usually 1-40%.

According to one embodiment of the present invention, there is no particular limitation to the method for deriving said diene or said dienophile from said biomass material, and various methods commonly known in the art can be adopted. For example, 2,5-dimethylfuran can be derived from the biomass such as glucose, fructose, cellulose and 5-hydroxymethylfurfural through acid-catalysis and hydrogenation (Thananatthanachon T, Rauchfuss T B. Efficient Production of the Liquid Fuel 2,5-Dimethylfuran from Fructose Using Formic Acid as a Reagent[J]. Angewandte Chemie, 2010, 122 (37): 6766-6768; Huang Y B, Chen M Y, Yan L, et al. Nickel-Tungsten Carbide Catalysts for the Production of 2,5-Dimethylfuran from Biomass-Derived Molecules [J]. ChemSusChem, 2014, 7 (4): 1068-1072.). Alternatively, ethanol can be derived from the biomass such as seeweed, corn and lignocellulose through hydrolysis and fermentation, and have been used in the industry (A review on third generation bioethanol feedstock, Siti Azmah Jambo, Rahmath Abdulla, Siti Hajar Mohd Azhar, Hartinie Marbawi, Jualang Azlan Gansau, Pogaku Ravindra, Renewable and Sustainable Energy Reviews, Volume 65, November 2016, Pages 756-769; Prospects of bioethanol fuels E30 and E85 application in Russia and technical requirements for their quality, M. A. Ershov, E. V. Grigoreva, I. F. Habibullin, V. E. Emelyanov, D. M. Strekalina, Renewable and Sustainable Energy Reviews, Volume 66, December 2016, Pages 228-232). Therefore, the process for producing aromatic hydrocarbon according to the present invention can further comprise a step of a catalytic conversion of biomass material and an optional subsequent catalytic hydrogenation to produce said diene and/or said dienophile.

According to a preferable embodiment of the present invention, said catalyst can be a molecular sieve. As said molecular sieve, ZSM-type molecular sieve, Y-type molecular sieve, beta-type molecular sieve and MCM-type molecular sieve; particularly ZSM-5, Y-type molecular sieve, beta-type molecular sieve and MCM-41; More particularly ZSM-5 can be for example listed out. These molecular sieves can be used alone, or a combination of two or more can be used. These molecular sieves can be a commercially available product or can be prepared according to the prior art.

According to one embodiment of the present invention, as said ZSM-type molecular sieve, ZSM-5, ZSM-11, ZSM-22, ZSM-23 and ZSM-38, particularly ZSM-5 (or HZSM-5) can be listed out. Here, said ZSM-type molecular sieve has a SiO2/Al2O3 molar ratio of generally 10 to 500, preferably 15 to 200. Different kinds (including different SiO2/Al2O3 molar ratio) of ZSM-type molecular sieves can be used alone, or a combination of two or more can be used.

According to one embodiment of the present invention, as said Y-type molecular sieve, it has a SiO2/Al2O3 molar ratio of generally 2 to 80, preferably 3 to 50. Different kinds (including different SiO2/Al2O3 molar ratio) of Y-type molecular sieve can be used alone, or a combination of two or more can be used.

According to one embodiment of the present invention, as said beta-type molecular sieve, it has a SiO2/Al2O3 molar ratio of generally 10 to 150, preferably 15 to 65. Different kinds (including different SiO2/Al2O3 molar ratio) of beta-type molecular sieve can be used alone, or a combination of two or more can be used.

According to one embodiment of the present invention, as said MCM-type molecular sieve, MCM-22 and MCM-41 can be listed out. Here, said MCM-type molecular sieve has a SiO2/Al2O3 molar ratio of generally 20 to 250, preferably 40 to 150. Different kinds (including different SiO2/Al2O3 molar ratio) of MCM-type molecular sieve can be used alone, or a combination of two or more can be used.

According to one embodiment of the present invention, said molecular sieve is used in form of a molecular sieve composite, said molecular sieve composition contains: a1) 20 to 80 weight parts of said molecular sieve, b1) 20 to 80 weight parts of binder, and c1) 0 to 10 weight parts of adjuvant. Particularly, said molecular sieve composition contains: a1) 50 to 80 weight parts of said molecular sieve, b1) 20 to 50 weight parts of binder, and c1) 0.01 to 10 weight parts (or 0.01 to 5 weight parts) of adjuvant.

According to one embodiment of the present invention, these molecular sieve compositions can be made directly using commercially available products or according to methods known in the art. Specifically, a method for producing the molecular sieve composition includes, for example, a method of kneading a molecular sieve, a binder, and a co-extruding agent, a pore-expanding agent and water, as necessary, into a mixture, extruding the mixture into shape, drying at 100-200° C. for 24 hours, and then calcining at 400-700° C. for 1-10 hours. Examples of the co-extruding agent include those conventionally used in the field such as sesbania powder, polyethylene glycol or sodium carboxymethylcellulose, and examples of the pore-expanding agent include citric acid, oxalic acid or ethylenediaminetetraacetic acid and the like which are conventionally used in the art. Generally, the co-extruding agent and the pore-expanding agent are added in a total amount not higher than 10 wt % of the total weight of the mixture. If necessary, the acid may be added at the time of extruding into shape. Examples of the acid include an inorganic acid, an acetic acid or an aqueous solution thereof, and the like, particularly, an aqueous solution of nitric acid, sulfuric acid or phosphoric acid. Generally, an aqueous solution of an acid is added in an amount of 50-90 wt % of the total weight of said mixture.

According to one embodiment of the present invention, said adjuvant can be introduced during or after making said molecular sieve composition, or can be also introduced to said molecular sieve, and then the resulting molecular sieve is used to make said molecular sieve; there is no particular limit. As the introduction method of said adjuvant, for example, those conventionally used in the art can be listed out, in particular ion-exchanging method or impregnation method. In these methods, the adjuvant is generally used in the form of a precursor. As the precursor of the metal adjuvant, for example, nitrate, sulfate, acetate or chloride of the metal may be mentioned. Examples of the precursor of the boron adjuvant include boric acid and borax. Examples of precursors for phosphorus adjuvant include diammonium hydrogen phosphate and the like.

According to one embodiment of the present invention, examples of the binder include those conventionally used in the production of molecular sieve compositions in the art, and more specifically, silica sol, pseudo-boehmite, alumina, clay treated with acid, kaolin, montmorillonite and bentonite, particularly alumina (especially γ-alumina), pseudo-boehmite, silica sol and the like. These binders can be used alone, or a combination of two or more can be used.

According to one embodiment of the present invention, as said adjuvant, for example, the following can be listed out: Na, Ca, K, Be, Mg, Ba, V, Nb, Cr, Mo, W, Mn, Re, Fe, Co, Ni, Cu, Zn, Ga, Ru, Pd, Pt, Ag, B, Al, Sn, P, Sb, La and Ce, particularly Ca, K, Mg, Cr, Mo, Fe, Ni, Cu, Zn, Ga, Ru, Pd, Pt, Ag, B, Sn, P, La and Ce the like. These adjuvants can be used alone, or a combination of two or more can be used.

According to one embodiment of the present invention, as the molecular sieve, in particular M/ZSM-5 can be mentioned, wherein M is selected from Zn, Ga, Sn, or combinations thereof. The molecular sieve or the molecular sieve composition containing the molecular sieve is particularly suitable for use as a catalyst. The molecular sieves can be produced directly using commercially available products or by methods known in the art.

According to one embodiment of the present invention, the contacting step can be performed in one or more reactors. Examples of the reactor include a bed reactor, particularly a fixed bed reactor, a fluidized bed reactor, an ebullated bed reactor, or a combination thereof. In this case, the operation mode of the reactor may be either a batch manner or a continuous manner, and is not particularly limited.

According to one embodiment of the present invention, the contacting step can be carried out under an inert atmosphere or a reducing atmosphere. As the inert atmosphere, for example, it may include N2, CO2, He, Ar or combinations thereof. As the reducing atmosphere, for example, it can include CO, H2 or a combination thereof. In addition, the contacting step may be carried out in a mixed atmosphere of an inert atmosphere and a reducing atmosphere.

According to one embodiment of the present invention, with respect to the total weight of the aromatic hydrocarbon product, in weight percent, the content of BTX aromatic hydrocarbons (benzene, toluene and xylene) in the aromatic hydrocarbon product is typically 20-90 wt %, and the rest is non-aromatic and heavy aromatics.

After the aromatic hydrocarbon (i.e., the xylene-enriched aromatic hydrocarbon product) is produced by the process for producing aromatic hydrocarbons according to the present invention as described above, the p-xylene can be separated from the aromatic hydrocarbon product by separation. In view of the above, the present invention also relates to a process for producing p-xylene which comprises a step of producing aromatic hydrocarbon according to the process for producing an aromatic hydrocarbon according to the present invention; and a step of separating p-xylene from the aromatic hydrocarbon.

According to one embodiment of the present invention, the method of separating p-xylene from the aromatic hydrocarbon is not particularly limited, and those conventionally known in the art can be directly applied. Since the xylene content of the aromatic hydrocarbon obtained by the present invention is relatively enriched as compared with the aromatic hydrocarbons obtained by the prior art process, the separation process is characterized by a reduction in operating costs and a reduction in operational complexity. In general, after the separation of the aromatic hydrocarbon, a p-xylene product can be directly obtained with a purity of 70 to 99.9% by weight.

According to one embodiment of the present invention, terephthalic acid can be produced from the p-xylene produced according to the present invention as a raw material. In view of the above, the present invention also relates to a process for producing terephthalic acid which comprises the step of producing p-xylene according to the process for producing p-xylene according to the present invention; and the step of converting p-xylene into terephthalic acid.

According to one embodiment of the present invention, the method of converting p-xylene into terephthalic acid is not particularly limited and those conventionally known in the art can be directly used.

EXAMPLES

The present invention will be further discussed in detail with several examples, but the present invention is not limited by these examples.

In the context of this specification, the selectivity is calculated according to the following formula.

> The increase in the initial reaction activity ($\Delta C_{t=1}\%$)= the conversion rate of the reaction of Examples at 1 hour in which the alcohol is added as dienophile–the conversion rate of Comparative Example 1 at 1 hour in which ethylene is used as dienophile.

> 2,5-dimethylfuran conversion rate ($C$ %)=the mole of the residual 2,5-dimethylfuran after the reaction/the total mole of the added 2,5-dimethylfuran×100%.

> The increase in the reaction conversion rate ($\Delta C$ %)=the conversion rate of 2,5-dimethylfuran at the end of the reaction–the conversion rate of the reaction in which ethylene is used as dienophile.

> $P$-xylene selectivity ($Sel_x\%$)=the content of $p$-xylene in the product/the amount of the whole product×100%.

> The increase in the $p$-xylene selectivity ($\Delta Sel_x\%$)= the selectivity of Examples at 1 hour in which the alcohol is added as dienophile–the selectivity of Comparative Example 1 at 1 hour in which ethylene is used as dienophile.

> Dienophile ratio $R$=the mole of the added alcohol/ (the mole of the added alcohol+the mole of ethylene)×100%.

Example 1

35 g of fructose was dissolved in water to form an aqueous solution of fructose (35%), to which was added 2 wt % NaCl and 5 mL HCl solution (0.25 mol/L). The mixture was mixed evenly. 100 mL butanol was added as an extracting phase to extract the product. The mixture was reacted for 10 minutes at 180° C., and the ratio of the organic and aqueous phases was kept as a constant during the reaction. After the reaction, the obtained product was 5-hydroxymethyl furfural. Further, the compound was subjected to a hydrogenation at 220° C. and 6 atmospheres of hydrogen and a WHSV of 1.0 $h^{-1}$ under the RuCu/C catalyst. After the reaction, the resulting mixture was separated to produce 2,5-dimethyl furan.

1 g of the catalyst ZSM-5 was dried and dehydrated at 120° C. for 12 hours. The catalyst had a composition of 50 parts of ZSM-5 molecular sieve (with a SiO2/Al2O3 ratio=50), 50 part of alumina as binder. The reaction substrate was 20 ml of 2,5-dimethylfuran and 20 ml of ethanol. Before the reaction, the reactor was purged 5 times with N2. Afterwards, the reaction was conducted at 400° C. for 6 hours. The reaction pressure was an autogenous pressure. After the reaction, the reaction result was analyzed qualitatively with mass spectrum and quantitatively with chromatogram. The initial reaction activity was increased by 36%, the reaction substrate 2,5-dimethylfuran conversion rate was 96%, the reaction conversion rate was increased 42%, the p-xylene selectivity was 85%, the p-xylene selectivity was increased by 37%. The reaction product composition was shown in Table 1.

TABLE 1

| | component | | | | | | | | |
|---|---|---|---|---|---|---|---|---|---|
| | non-aromatics | benzene | toluene | ethyl benzene | p-xylene | m-xylene | o-xylene | C9 aromatics | C10 + aromatics |
| content/wt % | 14 | 0 | 0 | 0 | 85 | 0 | 0 | 0 | 1 |

Example 2

1 g of the catalyst MCM-41 was dried and dehydrated at 120° C. for 12 hours. The catalyst had a composition of 50 parts of MCM-41 molecular sieve (with a SiO2/Al2O3 ratio=100), 50 part of alumina as binder. The reaction substrate was 20 ml of 2,5-dimethylfuran+200 ml of ethanol. Before the reaction, the reactor was purged 5 times with H2. The gas pressure was kept at 0.1 MPa. Afterwards, the reaction was conducted at 250° C. for 6 hours. The reaction pressure was an autogenous pressure. After the reaction, the reaction result was analyzed qualitatively with mass spectrum and quantitatively with chromatogram. The initial reaction activity was increased by 23%, the reaction substrate 2,5-dimethylfuran conversion rate was 83%, the reaction conversion rate was increased 29%, the p-xylene selectivity was 78%, the p-xylene selectivity was increased by 30%. The reaction product composition was shown in Table 2.

TABLE 2

| | component | | | | | | | | |
|---|---|---|---|---|---|---|---|---|---|
| | non-aromatics | benzene | toluene | ethyl benzene | p-xylene | m-xylene | o-xylene | C9 aromatics | C10 + aromatics |
| content/wt % | 22 | 0 | 0 | 0 | 78 | 0 | 0 | 0 | 0 |

Example 3

50 g of fructose was added to 60 ml of formic acid. After mixing, the resulting mixture was stirred at 150° C. for 2 hours. The resulting brown mixture was cooled to room temperature. Afterwards, the mixture was diluted with 150 ml of tetrahydrofuran. 5 ml of sulfuric acid and 4 g of Pd/C catalyst were continuously added. The resulting mixture was continuously stirred at 70° C. for 10 hours. Afterwards, the mixture was filtered, diluted with 200 ml of water, extracted with 170 ml of ethyl ether for 3 times. The resulting extracts were combined and rotary-vaporized to produce 2,5-dimethylfuran.

1 g of the catalyst Y was dried and dehydrated at 120° C. for 12 hours. The catalyst had a composition of 60 parts of Y molecular sieve (with a SiO2/Al2O3 ratio=6), 40 part of alumina as binder. The reaction substrate was 30 ml of 2,5-dimethylfuran+100 ml of a mixture of ethanol and sec-butanol, the mixing ratio of ethanol to sec-butanol was 9:1. Before the reaction, the reactor was purged 5 times with N2. Afterwards, the reaction was conducted at 340° C. for 6 hours. The reaction pressure was an autogenous pressure. After the reaction, the reaction result was analyzed qualitatively with mass spectrum and quantitatively with chromatogram. The initial reaction activity was increased by 37%, the reaction substrate 2,5-dimethylfuran conversion rate was 96%, the reaction conversion rate was increased 42%, the p-xylene selectivity was 86%, the p-xylene selectivity was increased by 38%. The reaction product composition was shown in Table 3.

TABLE 3

| | component | | | | | | | | |
|---|---|---|---|---|---|---|---|---|---|
| | non-aromatics | benzene | toluene | ethyl benzene | p-xylene | m-xylene | o-xylene | C9 aromatics | C10 + aromatics |
| content/wt % | 22 | 0 | 0 | 0 | 86 | 0 | 0 | 0 | 2 |

Example 4

1 g of the catalyst Y was dried and dehydrated at 120° C. for 12 hours. The catalyst had a composition of 65 parts of Y molecular sieve (with a SiO2/Al2O3 ratio=70), 35 part of alumina as binder. The reaction substrate was 150 ml of 2,5-dimethylfuran+750 ml of ethanol. Before the reaction, the reactor was purged 5 times with N2. Afterwards, the reaction was conducted at 180° C. for 8 hours. The reaction pressure was an autogenous pressure. After the reaction, the reaction result was analyzed qualitatively with mass spectrum and quantitatively with chromatogram. The initial reaction activity was increased by 40%, the reaction substrate 2,5-dimethylfuran conversion rate was 99%, the reaction conversion rate was increased 45%, the p-xylene selectivity was 87%, the p-xylene selectivity was increased by 39%. The reaction product composition was shown in Table 4.

TABLE 4

| | component | | | | | | | | |
|---|---|---|---|---|---|---|---|---|---|
| | non-aromatics | benzene | toluene | ethyl benzene | p-xylene | m-xylene | o-xylene | C9 aromatics | C10 + aromatics |
| content/wt % | 13 | 0 | 0 | 0 | 87 | 0 | 0 | 0 | 0 |

Example 5

20 g of the catalyst ZSM-5 was dried and dehydrated at 120° C. for 12 hours. The catalyst had a composition of 10 parts of ZSM-5 molecular sieve (with a SiO2/Al2O3 ratio=300), 90 part of alumina as binder. The reaction substrate was 40 ml of 2-methylfuran+40 ml of isopropanol. Before the reaction, the reactor was purged 5 times with N2. Afterwards, the reaction was conducted at 350° C. for 6 hours. The reaction pressure was an autogenous pressure. After the reaction, the reaction result was analyzed qualitatively with mass spectrum and quantitatively with chromatogram. The initial reaction activity was increased by 34%, the reaction substrate 2,5-dimethylfuran conversion rate was 93%, the reaction conversion rate was increased 39%, the p-xylene selectivity was 78%, the p-xylene selectivity was increased by 30%. The reaction product composition was shown in Table 5.

TABLE 5

| | component | | | | | | | | |
|---|---|---|---|---|---|---|---|---|---|
| | non-aromatics | benzene | toluene | ethyl benzene | p-xylene | m-xylene | o-xylene | C9 aromatics | C10 + aromatics |
| content/wt % | 20 | 0 | 0 | 0 | 10 | 28 | 40 | 0 | 2 |

Example 6

1 g of the catalyst MCM-22 was dried and dehydrated at 120° C. for 12 hours. The catalyst had a composition of 40 parts of MCM-22 molecular sieve (with a SiO2/Al2O3 ratio=150), 60 part of alumina as binder. The reaction substrate was 20 ml of 2-methylfuran+20 ml of isopropanol. Before the reaction, the reactor was purged 5 times with CO2. The gas pressure was kept at 5 Mpa. Afterwards, the reaction was conducted at 100° C. for 26 hours. The reaction pressure was an autogenous pressure. After the reaction, the reaction result was analyzed qualitatively with mass spectrum and quantitatively with chromatogram. The initial reaction activity was increased by 36%, the reaction substrate 2,5-dimethylfuran conversion rate was 95%, the reaction conversion rate was increased 41%, the p-xylene selectivity was 83%, the p-xylene selectivity was increased by 35%. The reaction product composition was shown in Table 6.

TABLE 6

| | component | | | | | | | | |
|---|---|---|---|---|---|---|---|---|---|
| | non-aromatics | benzene | toluene | ethyl benzene | p-xylene | m-xylene | o-xylene | C9 aromatics | C10 + aromatics |
| content/wt % | 17 | 0 | 0 | 0 | 1 | 33 | 49 | 0 | 0 |

Example 7

1 g of the catalyst Y was dried and dehydrated at 120° C. for 12 hours. The catalyst had a composition of 50 parts of Y molecular sieve (with a SiO2/Al2O3 ratio=25), 50 part of alumina as binder. The reaction substrate was 40 ml of 2-methylfuran+4 ml of isopropanol. Before the reaction, the reactor was purged 5 times with N2. Afterwards, the reaction was conducted at 280° C. for 6 hours. The reaction pressure was an autogenous pressure. After the reaction, the reaction result was analyzed qualitatively with mass spectrum and quantitatively with chromatogram. The initial reaction activity was increased by 32%, the reaction substrate 2,5-dimethylfuran conversion rate was 91%, the reaction conversion rate was increased 37%, the p-xylene selectivity was 82%, the p-xylene selectivity was increased by 34%. The reaction product composition was shown in Table 7.

TABLE 7

| | component | | | | | | | | |
|---|---|---|---|---|---|---|---|---|---|
| | non-aromatics | benzene | toluene | ethyl benzene | p-xylene | m-xylene | o-xylene | C9 aromatics | C10 + aromatics |
| content/wt % | 18 | 0 | 0 | 0 | 8 | 26 | 48 | 0 | 0 |

Example 8

1 g of the catalyst ZSM-5 was dried and dehydrated at 120° C. for 12 hours. The catalyst had a composition of 55 parts of ZSM-5 molecular sieve (with a SiO2/Al2O3 ratio=150), 45 part of alumina as binder. The reaction substrate was 40 ml of 2-methylfuran+40 ml of isopropanol. Before the reaction, the reactor was purged 5 times with N2. A mixed gas of hydrogen and nitrogen (1:1) was used. The gas pressure was kept at 1 Mpa. Afterwards, the reaction was conducted at 250° C. for 8 hours. The reaction pressure was an autogenous pressure. After the reaction, the reaction result was analyzed qualitatively with mass spectrum and quantitatively with chromatogram. The initial reaction activity was increased by 21%, the reaction substrate 2,5-dimethylfuran conversion rate was 83%, the reaction conversion rate was increased 29%, the p-xylene selectivity was 78%, the p-xylene selectivity was increased by 30%. The reaction product composition was shown in Table 8.

TABLE 8

| | component | | | | | | | | |
|---|---|---|---|---|---|---|---|---|---|
| | non-aromatics | benzene | toluene | ethyl benzene | p-xylene | m-xylene | o-xylene | C9 aromatics | C10 + aromatics |
| content/wt % | 22 | 0 | 0 | 0 | 4 | 27 | 47 | 0 | 0 |

Example 9

2 g of the catalyst (ZSM-5) was dried and dehydrated at 120° C. for 12 hours. The catalyst had a composition of 60 parts of ZSM-5 molecular sieve (with a SiO2/Al2O3 ratio=500), 40 part of alumina as binder. The reaction substrate was 40 ml of furan+100 ml of a mixture of ethanol+sec-butanol, wherein the mixing ratio of ethanol to sec-butanol being 1:1. Before the reaction, the reactor was purged 5 times with N2. Afterwards, the reaction was conducted at 400° C. for 6 hours. The reaction pressure was an autogenous pressure. After the reaction, the reaction result was analyzed qualitatively with mass spectrum and quantitatively with chromatogram. The initial reaction activity was increased by 20%, the reaction substrate 2,5-dimethylfuran conversion rate was 81%, the reaction conversion rate was increased 27%, the p-xylene selectivity was 83%, the p-xylene selectivity was increased by 35%. The reaction product composition was shown in Table 9.

TABLE 9

| | component | | | | | | | | |
|---|---|---|---|---|---|---|---|---|---|
| | non-aromatics | benzene | toluene | ethyl benzene | p-xylene | m-xylene | o-xylene | C9 aromatics | C10 + aromatics |
| content/wt % | 17 | 50 | 0 | 13 | 0 | 0 | 20 | 0 | 0 |

Example 10

36 g of fructose was added to 50 ml of formic acid. After mixing, the resulting mixture was stirred at 150° C. for 2 hours. The resulting brown mixture was cooled to room temperature. Afterwards, the mixture was diluted with 100 ml of tetrahydrofuran. 4 ml of sulfuric acid and 4 g of Pd/C catalyst were continuously added. The resulting mixture was continuously stirred at 70° C. for 10 hours. Afterwards, the mixture was filtered, diluted with 150 ml of water, extracted with 150 ml of ethyl ether for 3 times. The resulting extracts were combined and rotary-vaporized to produce 2,5-dimethylfuran.

2 g of the catalyst beta was dried and dehydrated at 120° C. for 12 hours. The catalyst had a composition of 50 parts of beta molecular sieve (with a SiO2/Al2O3 ratio=30), 50 part of alumina as binder. The reaction substrate was 40 ml of 2,5-dimethylfuran+40 ml of ethanol. Before the reaction, the reactor was purged 5 times with N2. Afterwards, the reaction was conducted at 300° C. for 5 hours. The reaction pressure was an autogenous pressure. After the reaction, the reaction result was analyzed qualitatively with mass spectrum and quantitatively with chromatogram. The initial reaction activity was increased by 33%, the reaction substrate 2,5-dimethylfuran conversion rate was 92%, the reaction conversion rate was increased 38%, the p-xylene selectivity was 78%, the p-xylene selectivity was increased by 30%. The reaction product composition was shown in Table 10.

TABLE 10

| | component | | | | | | | | |
|---|---|---|---|---|---|---|---|---|---|
| | non-aromatics | benzene | toluene | ethyl benzene | p-xylene | m-xylene | o-xylene | C9 aromatics | C10 + aromatics |
| content/wt % | 22 | 0 | 0 | 0 | 78 | 0 | 0 | 0 | 0 |

Example 11

1 g of the catalyst beta was dried and dehydrated at 120° C. for 12 hours. The catalyst had a composition of 40 parts of beta molecular sieve (with a SiO2/Al2O3 ratio=100), 60 part of alumina as binder. The reaction substrate was 20 ml of 2,5-dimethylfuran+20 ml of ethanol. Before the reaction, the reactor was purged 5 times with N2. Afterwards, the reaction was conducted at 250° C. for 6 hours. The reaction pressure was an autogenous pressure. After the reaction, the reaction result was analyzed qualitatively with mass spectrum and quantitatively with chromatogram. The initial reaction activity was increased by 27%, the reaction substrate 2,5-dimethylfuran conversion rate was 87%, the reaction conversion rate was increased 33%, the p-xylene selectivity was 81%, the p-xylene selectivity was increased by 33%. The reaction product composition was shown in Table 11.

| | component | | | | | | | | |
|---|---|---|---|---|---|---|---|---|---|
| | non-aromatics | benzene | toluene | ethyl benzene | p-xylene | m-xylene | o-xylene | C9 aromatics | C10 + aromatics |
| content/wt % | 19 | 0 | 0 | 0 | 81 | 0 | 0 | 0 | 0 |

Example 12

2 g of the catalyst MCM-41 was dried and dehydrated at 120° C. for 12 hours. The catalyst had a composition of 50 parts of MCM-41 molecular sieve (with a SiO2/Al2O3 ratio=50), 50 part of alumina as binder. The reaction substrate was 30 ml of 2,5-dimethylfuran+15 ml of ethanol. Before the reaction, the reactor was purged 5 times with N2. Afterwards, the reaction was conducted at 300° C. for 6 hours. The reaction pressure was an autogenous pressure. After the reaction, the reaction result was analyzed qualitatively with mass spectrum and quantitatively with chromatogram. The initial reaction activity was increased by 30%, the reaction substrate 2,5-dimethylfuran conversion rate was 89%, the reaction conversion rate was increased 35%, the p-xylene selectivity was 82%, the p-xylene selectivity was increased by 34%. The reaction product composition was shown in Table 12.

TABLE 12

| | component | | | | | | | | |
|---|---|---|---|---|---|---|---|---|---|
| | non-aromatics | benzene | toluene | ethyl benzene | p-xylene | m-xylene | o-xylene | C9 aromatics | C10 + aromatics |
| content/wt % | 18 | 0 | 0 | 0 | 82 | 0 | 0 | 0 | 0 |

Example 13

1.5 g of the catalyst MCM-22 was dried and dehydrated at 120° C. for 12 hours. The catalyst had a composition of 50 parts of MCM-22 molecular sieve (with a SiO2/Al2O3 ratio=70), 50 part of alumina as binder. The reaction substrate was 80 ml of 2,5-dimethylfuran+20 ml of ethanol. Before the reaction, the reactor was purged 5 times with N2. Afterwards, the reaction was conducted at 330° C. for 3 hours. The reaction pressure was an autogenous pressure. After the reaction, the reaction result was analyzed qualitatively with mass spectrum and quantitatively with chromatogram. The initial reaction activity was increased by 23%, the reaction substrate 2,5-dimethylfuran conversion rate was 83%, the reaction conversion rate was increased 29%, the p-xylene selectivity was 85%, the p-xylene selectivity was increased by 37%. The reaction product composition was shown in Table 13.

TABLE 13

| | component | | | | | | | | |
|---|---|---|---|---|---|---|---|---|---|
| | non-aromatics | benzene | toluene | ethyl benzene | p-xylene | m-xylene | o-xylene | C9 aromatics | C10 + aromatics |
| content/wt % | 15 | 0 | 0 | 0 | 85 | 0 | 0 | 0 | 0 |

Example 14

50 g of fructose was added to 60 ml of formic acid. After mixing, the resulting mixture was stirred at 150° C. for 2 hours. The resulting brown mixture was cooled to room temperature. Afterwards, the mixture was diluted with 150 ml of tetrahydrofuran. 5 ml of sulfuric acid and 4 g of Pd/C catalyst were continuously added. The resulting mixture was continuously stirred at 70° C. for 10 hours. Afterwards, the mixture was filtered, diluted with 200 ml of water, extracted with 170 ml of ethyl ether for 3 times. The resulting extracts were combined and rotary-vaporized to produce 2,5-dimethylfuran.

1 g of the catalyst Y was dried and dehydrated at 120° C. for 12 hours. The catalyst had a composition of 60 parts of Y molecular sieve (with a SiO2/Al2O3 ratio=6), 40 part of alumina as binder. The reaction substrate was 30 ml of 2,5-dimethylfuran+a mixture of ethanol and ethylene, the mixture was equimolar to the added dimethylfuran, the mixing ratio of ethanol to ethylene was 9:1. Before the reaction, the reactor was purged 5 times with N2. Afterwards, ethanol and ethylene were added respectively, The reaction was conducted at 200° C. for 6 hours. After the reaction, the reaction result was analyzed qualitatively with mass spectrum and quantitatively with chromatogram. The initial reaction activity was increased by 31%, the reaction substrate 2,5-dimethylfuran conversion rate was 90%, the reaction conversion rate was increased 36%, the p-xylene selectivity was 81%, the p-xylene selectivity was increased by 33%. The reaction product composition was shown in Table 14. In this example, The reaction pressure (gauge) was 3.8 MPa, The reaction pressure in the reaction example in which ethanol was used was 3.4 MPa, and after adding 10 mol % of ethylene, the pressure was increased by 12%.

TABLE 14

| | component | | | | | | | | |
|---|---|---|---|---|---|---|---|---|---|
| | non-aromatics | benzene | toluene | ethyl benzene | p-xylene | m-xylene | o-xylene | C9 aromatics | C10 + aromatics |
| content/wt % | 13 | 0 | 3 | 0 | 81 | 0 | 0 | 0 | 3 |

Example 15

1 g of the catalyst Y was dried and dehydrated at 120° C. for 12 hours. The catalyst had a composition of 60 parts of Y-molecular sieve (with a SiO2/Al2O3 ratio=6), 40 part of alumina as binder. The reaction substrate was 30 ml of 2,5-dimethylfuran+a mixture of ethanol and ethylene, the mixture being equimolar to the added dimethylfuran, wherein ethanol and ethylene are in a mixing ratio of 5:5. Before the reaction, the reactor was purged 5 times with N2. Afterwards, ethanol and ethylene were added respectively, the reaction was conducted at 200° C. for 6 hours. After the reaction, the reaction result was analyzed qualitatively with mass spectrum and quantitatively with chromatogram. The initial reaction activity was increased by 21%, the reaction substrate 2,5-dimethylfuran conversion rate was 81%, the reaction conversion rate was increased 27%, the p-xylene selectivity was 74%, the p-xylene selectivity was increased by 26%. The reaction product composition was shown in Table 15. In this example, the reaction pressure (gauge) was 5.4 MPa, The reaction pressure in the reaction example in which ethanol was used was 3.4 MPa. The addition of 50 mol % of ethylene caused a pressure increase by 60%.

TABLE 15

| | component | | | | | | | | |
|---|---|---|---|---|---|---|---|---|---|
| | non-aromatics | benzene | toluene | ethyl benzene | p-xylene | m-xylene | o-xylene | C9 aromatics | C10 + aromatics |
| content/wt % | 21 | 0 | 2 | 0 | 74 | 0 | 0 | 0 | 3 |

Example 16

1 g of the catalyst Y was dried and dehydrated at 120° C. for 12 hours. The catalyst had a composition of 60 parts of Y molecular sieve (with a SiO2/Al2O3 ratio=6), 40 part of alumina as binder. The reaction substrate was 30 ml of 2,5-dimethylfuran+a mixture of ethanol and ethylene, the mixture being equimolar to the added dimethylfuran, wherein ethanol and ethylene are in a mixing ratio of 1:9. Before the reaction, the reactor was purged 5 times with N2. Afterwards, ethanol and ethylene were added respectively, The reaction was conducted at 200° C. for 6 hours. After the reaction, the reaction result was analyzed qualitatively with mass spectrum and quantitatively with chromatogram. The initial reaction activity was increased by 9%, the reaction substrate 2,5-dimethylfuran conversion rate was 69%, the reaction conversion rate was increased 15%, the p-xylene selectivity was 67%, the p-xylene selectivity was increased by 19%. The reaction product composition was shown in Table 16. In this example, the reaction pressure (gauge) was 7.0 MPa, The reaction pressure in the reaction example in which ethanol was used was 3.4 MPa, and after adding 90 mol % of ethylene, the pressure was increased by 107%.

TABLE 16

| | component | | | | | | | | |
|---|---|---|---|---|---|---|---|---|---|
| | non-aromatics | benzene | toluene | ethyl benzene | p-xylene | m-xylene | o-xylene | C9 aromatics | C10 + aromatics |
| content/wt % | 27 | 0 | 3 | 0 | 67 | 0 | 0 | 0 | 3 |

Example 17

1 g of the catalyst MCM-41 was dried and dehydrated at 120° C. for 12 hours. The catalyst had a composition of 50 parts of MCM-41 molecular sieve (with a SiO2/Al2O3 ratio=150), 50 part of alumina as binder. The reaction substrate was 20 ml of 2,5-dimethylfuran+100 ml of ethanol. Before the reaction, the reactor was purged 5 times with N2. Afterwards, the reaction was conducted at 200° C. for 5 hours. The reaction pressure was an autogenous pressure. After the reaction, the reaction result was analyzed qualitatively with mass spectrum and quantitatively with chromatogram. The initial reaction activity was increased by 24%, the reaction substrate 2,5-dimethylfuran conversion rate was 86%, the reaction conversion rate was increased 32%, the p-xylene selectivity was 76%, the p-xylene selectivity was increased by 28%. The reaction product composition was shown in Table 17.

TABLE 17

| | component | | | | | | | | |
|---|---|---|---|---|---|---|---|---|---|
| | non-aromatics | benzene | toluene | ethyl benzene | p-xylene | m-xylene | o-xylene | C9 aromatics | C10 + aromatics |
| content/wt % | 24 | 0 | 0 | 0 | 76 | 0 | 0 | 0 | 0 |

Comparative Example 1

1 g of the catalyst MCM-41 was dried and dehydrated at 120° C. for 12 hours MCM-41. The catalyst had a composition of 50 parts of MCM-41 molecular sieve (with a SiO2/Al2O3 ratio=150), 50 part of alumina as binder. The reaction substrate was 20 ml of 2,5-dimethylfuran in 20 mL of n-heptane. Before the reaction, nitrogen was used to purge the reactor for three times, and then the reactor was charged with 4 MPa ethylene. Afterwards, the reaction was conducted at 200° C. for 5 hours. After the reaction, the reaction result was analyzed qualitatively with mass spectrum and quantitatively with chromatogram. The reaction substrate 2,5-dimethylfuran conversion rate was 54%, the p-xylene selectivity was 48%. The reaction product composition was shown in Table 18.

TABLE 18

| | component | | | | | | | | |
|---|---|---|---|---|---|---|---|---|---|
| | non-aromatics | Benzene | toluene | ethyl benzene | p-xylene | m-xylene | o-xylene | C9 aromatics | C10 + aromatics |
| content/wt % | 52 | 0 | 0 | 0 | 48 | 0 | 0 | 0 | 0 |

TABLE 19

| Ex | Substrate | Reaction substrate Ratio | R (mol %) | Catalyst | SiO2/Al2O3 ratio | Increase in the initial reaction activity/% | Conversion Rate % | Increase of the conversion rate/% | p-xylene selectivity/% | Increase of p-xylene selectivity/% | Increase of the reaction pressure/% |
|---|---|---|---|---|---|---|---|---|---|---|---|
| 1 | 2,5-dimethylfuran + ethanol | 1:1 | 100 | ZSM-5 | 50 | 36 | 96 | 42 | 85 | 37 | — |
| 2 | 2,5-dimethylfuran + ethanol | 1:10 | 100 | MCM-41 | 100 | 23 | 83 | 29 | 78 | 30 | — |

TABLE 19-continued

| Ex | Substrate | Reaction substrate Ratio | R (mol %) | Catalyst | SiO2/Al2O3 ratio | Increase in the initial reaction activity/% | Conversion Rate % | Increase of the conversion rate/% | p-xylene selectivity/% | Increase of p-xylene selectivity/% | Increase of the reaction pressure/% |
|---|---|---|---|---|---|---|---|---|---|---|---|
| 3 | 2,5-dimethylfuran + (9:1 ethanol butanol mixture) | 3:10 | 100 | Y | 6 | 37 | 96 | 42 | 86 | 38 | — |
| 4 | 2,5-dimethylfuran + ethanol | 1:5 | 100 | Y | 70 | 40 | 99 | 45 | 87 | 39 | — |
| 5 | 2-methylfuran + propanol | 1:1 | 100 | ZSM-5 | 300 | 34 | 93 | 39 | 78 | 30 | — |
| 6 | 2-methylfuran + propanol | 1:1 | 100 | MCM-22 | 150 | 36 | 95 | 41 | 83 | 35 | — |
| 7 | 2-methylfuran + propanol | 10:1 | 100 | Y | 25 | 32 | 91 | 37 | 82 | 34 | — |
| 8 | 2-methylfuran + propanol | 1:1 | 100 | ZSM-5 | 150 | 21 | 83 | 29 | 78 | 30 | — |
| 9 | furan + (1:1 ethanol + sec-butanol) | 1:4 | 100 | ZSM-5 | 500 | 20 | 81 | 27 | 83 | 35 | — |
| 10 | 2,5-dimethylfuran + ethanol | 1:1 | 100 | beta | 30 | 33 | 92 | 38 | 78 | 30 | — |
| 11 | 2,5-dimethylfuran + ethanol | 1:1 | 100 | beta | 100 | 27 | 87 | 33 | 81 | 33 | — |
| 12 | 2,5-dimethylfuran + ethanol | 2:1 | 100 | MCM-41 | 50 | 30 | 89 | 35 | 82 | 34 | — |
| 13 | 2,5-dimethylfuran + ethanol | 4:1 | 100 | MCM-22 | 70 | 23 | 83 | 29 | 85 | 37 | — |
| 14 | 2,5-dimethylfuran + ethanol + ethylene | 1:1 | 90 | Y | 6 | 31 | 90 | 36 | 81 | 33 | 12 |
| 15 | 2,5-dimethylfuran + ethanol + ethylene | 1:1 | 50 | Y | 6 | 21 | 81 | 27 | 74 | 26 | 60 |
| 16 | 2,5-dimethylfuran + ethanol + ethylene | 1:1 | 10 | Y | 6 | 9 | 69 | 15 | 67 | 19 | 107 |
| 17 | 2,5-dimethylfuran + ethanol | 1:1 | 100 | MCM-41 | 150 | 24 | 86 | 32 | 76 | 28 | — |
| Comp Ex. 1 | 2,5-dimethylfuran + ethylene | — | — | MCM-41 | 150 | — | 54 | — | 48 | — | — |

The description of the preferred embodiment of the present invention has been presented for purposes of illustration and description, but is not intended to be exhaustive or to limit the invention to the form disclosed. It will be appreciated by those skilled in the art that changes could be made to the embodiment described above without departing from the broad inventive concept thereof. It is understood, therefore, that this invention is not limited to the particular embodiment disclosed, but covers modifications within the spirit and scope of the present invention as defined by the appended claims.

The invention claimed is:

1. A process for preparing an aromatic hydrocarbon, comprising a step of reacting a reaction mixture comprising a diene, an alcohol, and optionally an olefin in the presence of a catalyst to produce a product mixture comprising aromatic hydrocarbons, wherein a molar percentage of said alcohol is 5-100 mol % of a total amount of said olefin and said alcohol, wherein said diene is of formula (I):

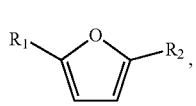

wherein $R_1$ and $R_2$ are identical or different, and are selected from a group consisting of hydrogen, an optionally substituted C1-20 linear or branched alkyl, an optionally substituted C2-20 linear or branched alkenyl, an optionally substituted C2-20 linear or branched alkynyl, an optionally substituted C3-20 cycloalkyl and an optionally substituted C6-20 aryl respectively and independently, said olefin is selected from C2-C10 olefins and mixtures thereof, and said alcohol is selected from C2-C10 alcohols and mixtures thereof, and wherein said catalyst comprises 20 to 80 weight parts of a molecular sieve, 20 to 80 weight parts of a binder, and 0 to 10 weight parts of an adjuvant, wherein the molecular sieve is selected from the group consisting of ZSM-type molecular sieve, Y-type molecular sieve, beta-type molecular sieve, MCM-type molecular sieve, and combinations thereof, the binder is selected from the group consisting of silica sol, pseudo-boehmite, alumina, acid-treated clay, kaolin, montmorillonite, bentonite, combinations thereof, and the adjuvant comprises Na, Ca, K, Be, Ba, V, Nb, Mo, W, Mn, Re, Ga, Ru, Pd, Pt, Ag, B, Sn, P, Sb, Ce or a combination of two or more thereof.

2. The process according to claim 1, wherein said ZSM-type molecular sieve has a $SiO_2/Al_2O_3$ molar ratio of 10-500, said Y-type molecular sieve has a $SiO_2/Al_2O_3$ molar ratio of 2-80, said beta-type molecular sieve has a $SiO_2/Al_2O_3$ molar ratio of 10-150, said MCM-type molecular sieve has a $SiO_2/Al_2O_3$ molar ratio of 20-250.

3. The process according to claim 1, wherein a molar ratio of said diene to the total of said alcohol and said olefin is 0.1-10.

4. The process according to claim 1, wherein said reacting step is conducted at a reaction temperature of 80 to 400° C. and under a reaction pressure of 0.5 to 10 MPa.

5. The process according to claim 1, wherein said reacting step is conducted at a predetermined reaction pressure, and said reaction pressure decreases as the molar percentage of said alcohol in the total amount of said olefin and said alcohol increases.

6. The process according to claim 1, wherein said diene and/or said alcohol is derived from a biomass material selected from the group consisting of xylitol, glucose, cellobiose, cellulose, hemicellulose, lignin, paper sludge, waste paper, sugar cane bagasse, glucose, wood, corn cobs, corn stalks, rice straw, and mixtures thereof.

7. The process according to claim 1, further comprising catalytically converting and optionally catalytically hydrogenating the biomass material to produce said diene and/or said alcohol.

8. A process for producing p-xylene, comprising:
producing aromatic hydrocarbons according to the process of claim 1; and
separating p-xylene from said aromatic hydrocarbons.

9. A process for producing terephthalic acid, comprising:
producing p-xylene according to the process of claim 8; and
converting p-xylene to terephthalic acid.

10. The process according to claim 3, wherein the molar percentage of said alcohol is 50 mol % or more of the total amount of said olefin and said alcohol.

11. The process according to claim 3, wherein the molar percentage of said alcohol is 90 mol % or more of the total amount of said olefin and said alcohol.

12. The process according to claim 1, wherein $R_1$ and $R_2$ are identical or different, and are selected from a group consisting of hydrogen, an optionally substituted C1-5 linear or branched alkyl, and an optionally substituted C2-10 linear or branched alkenyl.

13. The process according to claim 1, wherein $R_1$ and $R_2$ are both methyl.

14. The process according to claim 1, wherein said olefin is selected from the group consisting of C2-C10 α-olefins and mixtures thereof.

15. The process according to claim 1, wherein said olefin is ethylene, propene, or a mixture thereof.

16. The process according to claim 1, wherein said alcohol is selected from the group consisting of C2-C4 alcohols and mixtures thereof.

17. The process according to claim 1, wherein said alcohol is selected from the group consisting of ethanol, n-propanol, isopropanol, sec-butanol, and mixtures thereof.

18. The process according to claim 1, wherein said catalyst comprises 20 to 80 weight parts of the molecular sieve, and 20 to 80 weight parts of the binder.

19. The process according to claim 1, wherein the molar percentage of said alcohol is 100 mol % of the total amount of said olefin and said alcohol.

* * * * *